US007211263B2

(12) United States Patent
Guiso-Maclouf (10) Patent No.: US 7,211,263 B2
(45) Date of Patent: *May 1, 2007

(54) **USE OF ADENYLATE CYCLASE OR BACTERIA PRODUCING IT AS VACCINES AGAINST *BORDETELLA***

(75) Inventor: Nicole Guiso-Maclouf, Paris (FR)

(73) Assignee: Institut Pasteur, Paris Cedex 15 (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/334,796

(22) Filed: Jan. 2, 2003

(65) Prior Publication Data

US 2003/0224003 A1 Dec. 4, 2003

Related U.S. Application Data

(60) Division of application No. 09/771,599, filed on Jan. 30, 2001, now abandoned, which is a continuation of application No. 07/926,021, filed on Aug. 7, 1992, now Pat. No. 6,214,356, which is a continuation of application No. 07/623,706, filed as application No. PCT/FR90/00337 on May 11, 1990, now abandoned.

(30) Foreign Application Priority Data

May 12, 1989 (FR) .................................. 89 06321

(51) Int. Cl.
- A61K 39/10 (2006.01)
- A61K 39/02 (2006.01)
- A61K 39/00 (2006.01)
- A61K 39/38 (2006.01)
- A61K 38/43 (2006.01)
- A61K 38/00 (2006.01)
- A01N 37/18 (2006.01)

(52) U.S. Cl. .............................. 424/240.1; 424/184.1; 424/254.1; 424/253.1; 424/234.1; 424/236.1; 514/2; 530/300; 530/350

(58) Field of Classification Search ............. 424/254.1, 424/240.1, 184.1, 234.1, 253.1, 190.1, 93.1, 424/93.3, 236.1, 94.1; 530/300, 350; 514/2, 514/44

See application file for complete search history.

(56) References Cited

U.S. PATENT DOCUMENTS

| 4,652,521 A | 3/1987 | Confer et al. |
|---|---|---|
| 5,095,094 A | 3/1992 | Brezin et al. |
| 5,183,745 A | 2/1993 | Danchin et al. |
| 5,237,052 A | 8/1993 | Novotny |
| 5,438,120 A | 8/1995 | Novotny |
| 5,595,901 A | 1/1997 | Rocancourt et al. |
| 5,648,080 A | 7/1997 | Novotny |
| 5,786,189 A | 7/1998 | Locht et al. |
| 5,939,064 A | 8/1999 | Savelkoul et al. |
| 5,976,544 A | 11/1999 | Charles et al. |
| 5,985,286 A | 11/1999 | Gueirard et al. |
| 6,030,625 A | 2/2000 | Gueirard et al. |
| 6,040,427 A | 3/2000 | Locht et al. |
| 6,048,700 A | 4/2000 | Novotny et al. |
| 6,127,151 A | 10/2000 | Novotny et al. |
| 6,210,685 B1 | 4/2001 | Novotny et al. |
| 6,214,356 B1 * | 4/2001 | Guiso-Maclouf ........ 424/254.1 |
| 6,284,256 B1 | 9/2001 | Savelkoul et al. |
| 6,309,648 B1 | 10/2001 | Betsou et al. |
| 6,372,227 B1 | 4/2002 | Garcon et al. |
| 6,387,377 B1 | 5/2002 | Gueirard et al. |
| 6,399,076 B2 * | 6/2002 | Vose et al. ............... 424/254.1 |
| 6,964,767 B2 * | 11/2005 | Guiso-Maclouf et al. ....................... 424/184.1 |
| 7,070,779 B2 * | 7/2006 | Boursaux-Eude et al. ....................... 424/184.1 |
| 2002/0172691 A1 * | 11/2002 | Guiso-Maclouf ........ 424/254.1 |
| 2003/0108572 A1 * | 6/2003 | Novotny et al. ......... 424/237.1 |
| 2003/0224003 A1 * | 12/2003 | Guiso-Maclouf ........ 424/184.1 |
| 2006/0008474 A1 * | 1/2006 | Boursaux-Eude et al. ....................... 424/240.1 |

FOREIGN PATENT DOCUMENTS

| EP | 0 267 998 | 5/1988 |
|---|---|---|
| EP | 0 272 174 | 6/1988 |
| EP | 0 301 954 | 2/1989 |
| EP | 0338170 A1 * | 10/1989 |
| EP | 1188446 | 3/2002 |
| FR | 2 606 789 | 5/1988 |
| FR | 2 621 597 | 4/1989 |
| WO | WO 9013312 | 11/1990 |

OTHER PUBLICATIONS

Musser et al, J. Bacteriology, 1986, 166/1: 230-237.*
Watanbe et al, Infection and Immunity, 2003, 71/2: 733-738.*
Kourova et al, J. Clinical Microbiology, 2003, 41/8:3706-3711.*
Parkhill et al, Nat. Genet., 2003, 35/1:32-40 Abstract Only.*
Kawai et al, Scand. J. Infect. Dis., 1996, 28/4:377-381 Abstract Only.*
Liese et al, Archives of Disease in Childhood, 2003, 88:684-687 Abstract Only.*
Bergfors et al, Int. J. Infect. Dis., 1999 Spring, 3/3:140-146 Abstract Only.*

(Continued)

*Primary Examiner*—Nita Minnifield
(74) *Attorney, Agent, or Firm*—Finnegan, Henderson, Farabow, Garrett & Dunner, L.L.P.

(57) ABSTRACT

The invention relates to a method of immunizing a mammal against infection by a first *Bordetella* species. The method comprises administering to the mammal a preparation comprising a portion of the amino acid sequence of mature adenylate cyclase of a second *Bordetella* species. The invention also relates to vaccine preparations comprising a portion of the amino acid sequence of mature adenylate cyclase from *Bordetella* species.

5 Claims, 12 Drawing Sheets

OTHER PUBLICATIONS

He et al, JAMA, 1998, 280/7:635-637 Abstract Only.*
Hozbor et al, Current Microbiology, 1999, 38/5:273-278 Abstract Only.*
Parkhill et al, Nature Genetics, Sep. 2003, 35/1:32-40.*
Simsova et al, Int. J. Med. Micrbiol, 2004, 293:571-576.*
Strobel et al, J. Mol. Biol., 2003, 332:1-7.*
Ladant et al, Trends in Microbiology, Apr. 1999, 7/4:172-176.*
Vojtova et al, Current Opinion in Microbiology, 2006, 9:69-75.*
Ahuja et al, Critical Reviews in Microbiology, 2004, 30:187-196.*
Novotny et al., Develop. Biol. Std., vol. 61, pp. 27-41, 1985.
Hewlett et al., Soluble HA from Culture Medium of *Bordetella pertussis*: Purification and Char., J. of Bact., vol. 724, p. 890-898.
Robinson, A., Vaccine, vol. 3, pp. 11-22, Mar. 1985.
Robinson, A., Infection & Immunity, May 1983, 40(2), pp. 523-528.
Glaser et al., Molecular Microbiology, 2:19-30, 1988.
Guiso et al., Microbiol. Pathogenesis 7:373-380, 1989.
Ladant et al., J. of Biol. Chem. 261:16264-16269, 1986.
Novotny et al., J. of Infec. Disease 164: 114-22, 1991.
Novotny et al., Inf. & Immun. 50:199-206, 1985 (Abstract only).
Basset et al., Infection & Immun., 68/4: 1934-1941, Apr. 2000.
Khelef et al., Infection & Immun., 61/2: 486-490, Feb. 1993.
Mills et al., Infection & Immun., 61/2: 399-410, Feb. 1993.
Mills et al., Infection & Immun., 66/2: 594-602, Feb. 1998.
Kendrick et al., Am. J. Public Health, 37/7: 803-810, Jul. 1947.
Guiso, et al., Proceedings of 6$^{th}$ *Pertussis* Mtg., pp. 207-211, 1990.
Brezin, et al., FEMS Microbiology Letters 42: 75-80, 1987.
Romanos, et al., "Recombinant *Bordetella pertussis* pertactin (P69) from the yeast *Pichia pastoris*: high-level production and immunological properties," Vaccine, vol. 9, pp. 901-906, Dec. 1991.

* cited by examiner

GAAGCCTTGTTCTTCTTTTCATTAGAAAGAAATATGCGCTTTGTGTTTAGGATGATTTTC

-200

CTGTCCGAGTAGGGTGGATCCAAATTTTCCGGATTGGTGGGAATTTGTGCATTTTCACTG

CGAATGTTGGAATAATTTCGCCCATCGTCATACGACATGCTGGATGTTTGGTTCTTGCAG

-100

AAGGATGAGGTTCTGAGCGCTACACACCGGTTGCGTCGGTGCGAATCCGTTCAATCGACT

MetGlnGlnSerHisGlnAlaGlyTyrAlaAsnAlaAlaAsp
ACTTATCGACAGATCCACATGCAGCAATCGCATCAGGCTGGTTACGCAAACGCCGCCGAC

0
ArgGluSerGlyIleProAlaAlaValLeuAspGlyIleLysAlaValAlaLysGluLys
CGGGAGTCTGGCATCCCCGCAGCCGTACTCGATGGCATCAAGGCCGTGGCGAAGGAAAAA

100

AsnAlaThrLeuMetPheArgLeuValAsnProHisSerThrSerLeuIleAlaGluGly
AACGCCACATTGATGTTCCGCCTGGTCAACCCCCATTCCACCAGCCTGATTGCCGAAGGG

ValAlaThrLysGlyLeuGlyValHisAlaLysSerSerAspTrpGlyLeuGlnAlaGly
GTGGCCACCAAAGGATTGGGCGTGCACGCCAAGTCGTCCGATTGGGGGTTGCAGGCGGGC

200

TyrIleProValAsnProAsnLeuSerLysLeuPheGlyArgAlaProGluValIleAla
TACATTCCCGTCAACCCGAATCTTTCCAAACTGTTCGGCCGTGCGCCCGAGGTGATCGCG

FIG. 1A

ArgAlaAspAsnAspValAsnSerSerLeuAlaHisGlyHisThrAlaValAspLeuThr
CGGGCCGACAACGACGTCAACAGCAGCCTGGCGCATGGCCATACCGCGGTCGACCTGACG
.            300        .         .         .         .

LeuSerLysGluArgLeuAspTyrLeuArgGlnAlaGlyLeuValThrGlyMetAlaAsp
CTGTCGAAAGAGCGGCTTGACTATCTGCGGCAAGCGGGCCTGGTCACCGGCATGGCCGAT
.         .         .         .         .        400

GlyValValAlaSerAsnHisAlaGlyTyrGluGlnPheGluPheArgValLysGluThr
GGCGTGGTCGCGAGCAACCACGCAGGCTACGAGCAGTTCGAGTTTCGCGTGAAGGAAACC
.         .         .         .         .         .

SerAspGlyArgTyrAlaValGlnTyrArgArgLysGlyGlyAspAspPheGluAlaVal
TCGGACGGGCGCTATGCCGTGCAGTATCGCCGCAAGGGCGGCGACGATTTCGAGGCGGTC
.         .         .          500       .         .

LysValIleGlyAsnAlaAlaGlyIleProLeuThrAlaAspIleAspMetPheAlaIle
AAGGTGATCGGCAATGCCGCCGGTATTCCACTGACGGCGGATATCGACATGTTCGCCATT
.         .         .         .         .         .         .

MetProHisLeuSerAsnPheArgAspSerAlaArgSerSerValThrSerGlyAspSer
ATGCCGCATCTGTCCAACTTCCGCGACTCGGCGCGCAGTTCGGTGACCAGCGGCGATTCG
.            600       .         .         .         .

ValThrAspTyrLeuAlaArgThrArgArgAlaAlaSerGluAlaThrGlyGlyLeuAsp
GTGACCGATTACCTGGCGCGCACGCGGCGGGCCGCCAGCGAGGCCACGGGCGGCCTGGAT
.         .         .         .         .        700

ArgGluArgIleAspLeuLeuTrpLysIleAlaArgAlaGlyAlaArgSerAlaValGly
CGCGAACGCATCGACTTGTTGTGGAAAATCGCTCGCGCCGGCGCCCGTTCCGCAGTGGGC
.         .         .         .         .         .         .

FIG. 1B

```
ThrGluAlaArgArgGlnPheArgTyrAspGlyAspMetAsnIleGlyValIleThrAsp
ACCGAGGCGCGTCGCCAGTTCCGCTACGACGGCGACATGAATATCGGCGTGATCACCGAT
       .           .           .      800        .           .

PheGluLeuGluValArgAsnAlaLeuAsnArgArgAlaHisAlaValGlyAlaGlnAsp
TTCGAGCTGGAAGTGCGCAATGCGCTGAACAGGCGGGCGCACGCCGTCGGCGCGCAGGAC
       .           .           .           .           .           .

ValValGlnHisGlyThrGluGlnAsnAsnProPheProGluAlaAspGluLysIlePhe
GTGGTCCAGCATGGCACTGAGCAGAACAATCCTTTCCCGGAGGCAGATGAGAAGATTTTC
      900          .           .           .           .           .

ValValSerAlaThrGlyGluSerGlnMetLeuThrARgGlyGlnLeuLysGluTyrIle
GTCGTATCGGCCACCGGTGAAAGCCAGATGCTCACGCGCGGGCAACTGAAGGAATACATT
       .           .           .           .           .     1000

GlyGlnGlnArgGlyGluGlyTyrValPheTyrGluAsnArgAlaTyrGlyValAlaGly
GGCCAGCAGCGCGGCGAGGGCTATGTCTTCTACGAGAACCGTGCATACGGCGTGGCGGGG
       .           .           .           .           .           .

LysSerLeuPheAspAsp GlyLeuGlyAlaAlaProGlyValProSerGlyArgSerLys
AAAAGCCTGTTCGACGAT GGGCTGGGAGCCGCGCCCGGCGTGCCGAGCGGACGTTCGAAG
       .           .     1100        .

PheSerProAspValLeuGluThrValProAlaSerProGlyLeuArgArgProSerLeu
TTCTCGCCGGATGTACTGGAAACGGTGCCGGCGTCACCCGGATTGCGGCGGCCGTCGCTG
       .           .           .           .           .           .

GlyAlaValGluArgGlnAspSerGlyTyrAspSerLeuAspGlyValGlySerArgSer
GGCGCAGTGGAACGCCAGGATTCCGGCTATGACAGCCTTGATGGGGTGGGATCGCGATCG
       .    1200         .           .           .
```

FIG. 1C

```
PheSerLeuGlyGluValSerAspMetAlaAlaValGluAlaAlaGluLeuGluMetThr
TTCTCGTTGGGCGAGGTGTCCGACATGGCCGCCGTGGAAGCGGCGGAACTGGAAATGACC
       .         .         .         .         .         1300

ArgGlnValLeuHisAlaGlyAlaArgGlnAspAspAlaGluProGlyValSerGlyAla
CGGCAAGTCTTGCACGCCGGGGCGCGGCAGGACGATGCCGAGCCGGGCGTGAGCGGTGCG
       .         .         .         .         .         .

SErAlaHisTrpGlyGlnArgAlaLeuGlnGlyAlaGlnAlaValAlaAlaAlaGlnArg
TCGGCGCACTGGGGGCAGCGGGCGCTGCAGGGCGCCCAGGCGGTGGCGGCGGCGCAGCGG
       .         .      1400        .         .         .

LeuValHisAlaIleAlaLeuMetThrGlnPheGlyArgAlaGlySerThrAsnThrPro
CTGGTTCATGCCATTGCCCTGATGACGCAATTCGGCCGGGCCGGTTCCACCAACACGCCG
       .         .         .         .         .         .

GlnGluAlaAlaSerLeuSerAlaAlaValPheGlyLeuGlyGluAlaSerSerAlaVal
CAGGAAGCGGCCTCGTTGTCGGCGGCCGTGTTCGGCTTGGGCGAGGCCAGCAGCGCCGTG
       .      1500        .         .         .         .

AlaGluThrValSerGlyPhePheArgGlySerSerArgTrpAlaGlyGlyPheGlyVal
GCCGAAACCGTGAGCGGTTTTTTCCGCGGGTCTTCGCGCTGGGCCGGCGGTTTCGGCGTG
       .         .         .         .         .         1600

AlaGlyGlyAlaMetAlaLeuGlyGly[lyIleAlaAlaAlaValGlyAlaGlyMet Ser
GCTGGCGGCGCGATGGCGCTGGGAGGCGGCATCGCCGCGGCCGTTGGCGCCGGGATGTCG
       .         .         .         .         .         .

LeuThrAspAspAlaProAlaGlyGlnLqsAlaAlaAlaGlyAlaGluIleAlaLeuGln
TTGACCGATGACGCGCCGGCCGGACAGAAGGCCGCCGCCGGCGCCGAGATCGCGCTGCAG
       .         .      1700        .         .
```

FIG. 1D

```
LeuThrGlyGlyThrValGluLeuAlaSerSerIleAlaLeuAlaLeuAlaAlaAlaArg
TTGACAGGTGGAACGGTCGAGCTGGCTTCTTCCATCGCGTTGGCGCTGGCCGCGGCGCGC
    .         .         .         .         .         .

GlyValThrSerGlyLeuGlnValAlaGlyAlaSerAlaGlyAlaAlaAlaGlyAlaLeu
GGCGTGACCAGCGGCTTGCAGGTGGCCGGGGCGTCGGCCGGGGCGGCTGCCGGCGCATTG
    .        1800        .         .         .         .

AlaAlaAlaLeuSerProMetGluIleTyrGlyLeuValGlnGlnSerHisTyrAlaAsp
GCCGCGGCGCTCAGTCCCATGGAGATCTACGGCCTGGTGCAGCAATCGCACTATGCGGAT
    .         .         .         .        1900        .

GlnLeuAspLysLeuAlaGlnGluSerSerAlaTyrGlyTyrGluGlyAspAlaLeuLeu
CAGCTGGACAAGCTGGCGCAGGAATCGAGCGCATACGGTTACGAGGGCGACGCCTTGCTG
    .         .         .         .         .         .

AlaGlnLeuTyrArgAspLysThrAlaAlaGluGlyAlaValAlaGlyValSerAlaVal
GCCCAGCTGTATCGCGACAAGACGGCCGCCGAGGGCGCCGTCGCCGGCGTCTCCGCCGTC
    .         .         .        2000        .         .

LeuSerThrValGlyAlaAlaValSerIleAlaAlaAlaAlaSerValValGlyAlaPro
CTGAGCACGGTGGGGGCGGCGGTGTCGATCGCCGCGGCGGCCAGCGTGGTAGGGGCCCCG
    .         .         .         .         .         .

ValAlaValValThrSerLeuLeuThrGlyAlaLeuAsnGlyIleLeuArgGlyValGln
GTGGCGGTGGTCACTTCCTTGCTGACCGGGGCTCTCAACGGCATCCTGCGCGGCGTGCAG
    .        2100        .         .         .         .

GlnProIleIleGluLysLeuAlaAsnAspTyrAlaArgLysIleAspGluLeuGlyGly
CAGCCCATCATCGAAAAGCTGGCCAACGATTACGCTCGCAAGATCGACGAGCTGGGCGGG
    .         .         .         .        2200
```

FIG. 1E

ProGlnAlaTyrPheGluLysAsnLeuGlnAlaArgHisGluGlnLeuAlaAsnSerAsp
CCGCAAGCGTACTTCGAGAAAAACCTGCAGGCGCGTCACGAACAACTGGCCAATTCGGAC

GlyLeuArgLysMetLeuAlaAspLeuGlnAlaGlyTrpAsnAlaSerSerValIleGly
GGCCTACGGAAAATGCTGGCCGACCTGCAGGCCGGTTGGAACGCCAGCAGCGTGATCGGG
                          2300

ValGlnThrThrGluIleSerLysSerAlaLJuGluLeuAlaAlaIleThrGlyAsnAla
GTGCAGACGACAGAGATCTCCAAGTCGGCGCTCGAACTGGCCGCCATTACCGGCAACGCG

AspAsnLeuLysSerValAspValPheValAspArgPheValGlnGlyGluArgValAla
GACAACCTGAAATCCGTCGACGTGTTCGTGGACCGCTTCGTCCAGGGCGAGCGGGTGGCC
        2400

GlnGlnProValValLeuAs-ValAlaAlaGlyGlyIleAspIleAlaSerArgLysGly
GGCCAGCCGGTGGTCCTCGACGTCGCCGCCGGCGGCATCGATATCGCCAGCCGCAAGGGC
                                              2500

GluArgProAlaLeuThrPneIleThrProLeuAlaAlaProGlyGluGluGlnArgArg
GAGCGGCCGGCGCTGACGTTCATCACGCCGCTGGCCGCGCCAGGAGAAGAGCAGCGCCGG

ARgThrLysThrGlyLysSerGluPheThrThrPheValGluIleValGlyLysGlnAsp
CGCACGAAAACGGGCAAGAGCGAATTCACCACATTCGTCGAGATCGTGGGCAAGCAGGAC
                    2600

ArgTrpArgIleArgAspGlyAlaAlaAspThrThrIleAspLeuAlaLysValValSer
CGCTGGCGCATCCGGGACGGCGCGGCCGACACCACCATCGATCTGGCCAAGGTGGTGTCG

FIG. 1F

```
GlnLeuValAspAlaAsnGlyValLeuLysHisSerIleLysLeuAspValIleGlyGly
CAACTGGTCGACGCCAATGGCGTGCTCAAGCACAGCATCAAACTGGATGTGATCGGCGGA
      .       2700        .        .        .        .
AspGlyAspAspValValLeuAlaAsnAlaSerArgIleHisTyrAspGlyGlyAlaGly
GATGGCGATGACGTCGTGCTTGCCAATGCTTCGCGCATCCATTATGACGGCGGCGCGGGC
      .        .        .        .        .       2800
ThrAsnThrValSerTyrAlaAlaLeuGlyArgGlnAspSerIleThrValSerAlaAsp
ACCAACACGGTCAGCTATGCCGCCCTGGGTCGACAGGATTCCATTACCGTGTCCGCCGAC
      .        .        .        .        .        .
GlyGluArgPheAsnValArgLysGlnLeuAsnAsnAlaAsnValTyrArgGluGlyVal
GGGGAACGTTTCAACGTGCGCAAGCAGTTGAACAACGCCAACGTGTATCGCGAAGGCGTG
      .        .        .       2900        .        .
AlaThrGlnThrThrAlaTyrGlyLysArgThrGluAsnValGlnTyrArgHisValGlu
GCTACCCAGACAACCGCCTACGGCAAGCGCACGGAGAATGTCCAATACCGCCATGTCGAG
      .        .        .        .        .        .
LeuAlaArgValGlyGlnValValGluValAspThrLeuGluHisValGlnHisIleIle
CTGGCCCGTGTCGGGCAAGTGGTGGAGGTCGACACGCTCGAGCATGTGCAGCACATCATC
      .       3000        .        .        .        .
GlyGlyalaGlyAsnAspSerIleThrGlyAsnAlaHisAspAsnPheLeuAlaGlyGly
GGCGGGGCCGGCAACGATTCGATCACCGGCAATGCGCACGACAACTTCCTAGCCGGCGGG
      .        .        .        .       3100
SerGlyAspAspArgLeuAspGlyGlyAlaGlyAsnAspThrLeuValGlyGlyGluGly
TCGGGCGACGACAGGCTGGATGGCGGCGCCGGCAACGACACCCTGGTTGGCGGCGAGGGC
      .        .        .        .        .        .
```

FIG. 1G

```
GlnAsnThrValIleGlyGlyAlaGlyAspAspValPheLeuGlnAspLeuGlyValTrp
CAAAACACGGTCATCGGCGGCGCCGGCGACGACGTATTCCTGCAGGACCTGGGGGTATGG
       .         .         .      3200          .          .
SerAsnGlnLeuAspGlyGlyAlaGlyValAspThrValLysTyrAsnValHisGlnPro
AGCAACCAGCTCGATGGCGGCGCGGGCGTCGATACCGTGAAGTACAACGTGCACCAGCCT
    .         .         .         .         .         .         .

SerGluGluArgLeuGluArgMetGlyAspThrGlyIleHisAlaAspLeuGlnLysGly
TCCGAGGAGCGCCTCGAACGCATGGGCGACACGGGCATCCATGCCGATCTTCAAAAGGGC
       .      3300         .         .         .         .
ThrValGluLysTrpProAlaLeuAsnLeuPheSerValAspHisValLysAsnIleGlu
ACGGTCGAGAAGTGGCCGGCCCTGAACCTGTTCAGCGTCGACCATGTCAAGAATATCGAG
    .         .         .         .      3400           .
AsnLeuHisGlySerArgLeuAsnAspArgIleAlaGlyAspAspGlnAspAsnGluLeu
AATCTGCACGGCTCCCGCCTAAACGACCGCATCGCCGGCGACGACCAGGACAACGAGCTC
       .         .         .         .         .         .

TrpGlyHisAspGlyAsnAspThrIleArgGlyArgGlyGlyAspAspIleLeuArgGly
TGGGGCCACGATGGCAACGACACGATACGCGGCCGGGGCGGCGACGACATCCTGCGCGGC
       .         .         .      3500          .         .
GlyLeuGlyLeuAspThrLeuTyrGlyGluAspGlyAsnAspIlePheLeuGlnAspAsp
GGCCTGGGCCTGGACACGCTGTATGGCGAGGACGGCAACGACATGTTCCTGCAGGACGAC
       .         .         .         .         .         .         .

GluThrValSerAspAspIleAspGlyGlyAlaGlyLeuAspThrValAspTyrSerAla
GAGACCGTCAGCGATGACATCGACGGCGGCGCGGGGCTGGACACCGTCGACTACTCCGCC
       .      3600         .         .         .         .
```

FIG. 1H

```
MetIleHisProGlyArgIleValAlaProHisGluTyrGlyPheGlyIleGluAlaAsp
ATGATCCATCCAGGCAGGATCGTTGCGCCGCATGAATACGGCTTCGGGATCGAGGCGGAC
         .         .         .         .         .
                                                 3700
LeuSerArgGluTrpValArgLysAlaSerAlaLeuGlyValAspTyrTyrAspAsnVal
CTGTCCAGGGAATGGGTGCGCAAGGCGTCCGCGCTGGGCGTGGACTATTACGATAATGTC
         .         .         .         .         .         .
ArgAsnValGluAsnValIleGlyThrSerMetLysAspValLeuIleGlyAspAlaGln
CGCAATGTCGAAAACGTCATCGGTACGAGCATGAAGGATGTGCTCATCGGCGACGCGCAA
         .         .         .
                           3800                   .         .
AlaAsnThrLeuMetGlyGlnGlyGlyAspAspThrValArgGlyGlyAspGlyAspAsp
GCCAATACCCTGATGGGCCAGGGCGGCGACGATACCGTGCGCGGCGGCGACGGCGATGAT
         .         .         .         .         .         .
LeuLeuPheGly-lyAspGlyAsnAspMetLeuTyrGlyAspAlaGlyAsnAspThrLeu
CTGCTGTTCGGCGGCGACGGCAACGACATGCTGTATGGCGACGCCGGCAACGACACCCTC
                   .
                 3900         .         .         .         .
TyrGlyGlyLeuGlyAspAspThrLeuGluGlyGlyAlaGlyAsnAspTrpPheGlyGly
TACGGGGGGCTGGGCGACGATACCCTTGAAGGCGGCGCGGGCAACGATTGGTTCGGCCAG
         .         .         .         .         .
                                                 4000
ThrGlnAlaArgGluHisAspValLeuArgGlyGlyAspGlyValAspThrValAspTyr
ACGCAGGCGCGCGAGCATGACGTGCTGCGCGGCGGAGATGGGGTGGATACCGTCGATTAC
         .         .         .         .         .         .
SerGlnThrGlyAlaHisAlaGlyIleAlaAlaGlyArgIleGlyLeuGlyIleLeuAla
AGCCAGACCGGCGCGCATGCCGGCATTGCCGCGGGTCGCATCGGGCTGGGCATCCTGGCT
         .         .         .
                           4100         .         .
```

FIG. 1I

```
ApLeuGlyAlaGlyArgValAspLysLeuGlyGluAlaGlySerSerAlaTyrAspThr
GACCTGGGCGCCGGCCGCGTCGACAAGCTGGGCGAGGCCGGCAGCAGCGCCTACGATACG
      .         .         .         .         .         .

ValSerGlyIleGluAsnValValGlyThrGluLeuAlaAspArgIleThrGlyAspAla
GTTTCCGGTATCGAGAACGTGGTGGGCACGGAACTGGCCGACCGCATCACGGGCGATGCG
      .        4200       .         .         .         .
GlnAlaAsnValLeuArgGlyAlaGlyGlyAlaAspValLeuAlaGlyGlyGluGlyAsp
CAGGCCAACGTGCTGCGCGGCGCGGGTGGCGCCGACGTGCTTGCGGGCGGCGAGGGCGAC
      .         .         .         .         .        4300
AspValLeuLeuGlyGlyAspGlyAspAspGlnLeuSerGlyAspAlaGlyArgAspArg
GATGTGCTGCTGGGCGGCGACGGCGACGACCAGCTGTCGGGCGACGCCGGACGCGATCGC
      .         .         .         .         .         .

LeuTyrGlyGluAlaGlyAspAspTrpPhePheGlnAspAlaAlaAsnAlaGlyAsnLeu
TTGTACGGCGAAGCCGGTGACGACTGGTTCTTCCAGGATGCCGCCAATGCCGGCAATCTG
      .         .         .        4400       .         .
LeuAspGlyGlyAspGlyArgAspThrValAspPheSerGlyProGlyArgGlyLeuAsp
CTCGACGGCGGCGACGGCCGCGATACCGTGGATTTCAGCGGCCCGGGCCGGGGCCTCGAC
      .         .         .         .         .         .

AlaGlyAlaLysGlyValPheLeuSerLeuGlyLysGlyPheAlaSerLeuMetAspGlu
GCCGGCGCAAAGGGCGTATTCCTGAGCTTGGGCAAGGGGTTCGCCAGCCTGATGGACGAA
      .        4500       .         .         .         .
ProGluThrSerAsnValLeuArgAsnIleGluAsnAlaValGlySerAlaArgAspAsp
CCCGAAACCAGCAACGTGTTGCGCAATATCGAGAACGCCGTGGGCAGCGCGCGTGATGAC
      .         .         .         .        4600
```

FIG. 1J

```
ValLeuIleGlyAspAlaGlyAlaAsnValLeuAsnGlyLeuAlaGlyAsnAspValLeu
GTGCTGATCGGCGACGCAGGCGCCAACGTCCTCAATGGCCTGGCGGGCAACGACGTGCTG
    .         .         .         .         .         .

SerGlyGlyAlaGlyAspAspValLeuLeuGlyAspGluIlySerAspLeuLeuSerGly
TCCGGCGGCGCTGGCGACGATGTGCTGCTGGGCGACGAGGGCTCGGACCTGCTCAGCGGC
    .         .         .       4700        .         .

AspAlaGlyAsnAspAspLeuPheGlyglyGlnGlyAspA þThrTyrLeuPheGlyVal
GATGCGGGCAACGACGATCTGTTCGGCGGGCAGGGCGATGATACTTATCTGTTCGGGGTC
    .         .         .         .         .         .

GlyTyrGlyH;sAspThrIleTyrGluSerGlyGlyGlyHisAspThrIleArgIleAsn
GGGTACGGGCACGACACGATCTACGAATCGGGCGGCGGCCATGACACCATCCGCATCAAC
    .       4800        .         .         .         .

AlaGlyAlaAspGlnLeuTrpPxeAlaArgGlnGlyAsnAspLeuGluIleArgIleLeu
GCGGGGGCGGACCAGCTGTGGTTCGCGCGCCAGGGCAACGACCTGGAGATCCGCATTCTC
    .         .         .         .        4900

GlyThrAspAspAlaLeuThrValHisAspTrpTyrArgAspAlaAspHisArgValGlu
GGCACCGACGATGCACTTACCGTGCACGACTGGTATCGCGACGCCGATCACCGGGTGGAA
    .         .         .         .         .         .

IleIleHisAlaAlaAsnGlnAlaValAspGlnAlaGlyIleGluLysLeuValGluAla
ATCATCCATGCCGCCAACCAGGCGGTAGACCAGGCAGGCATCGAAAAGCTGGTCGAGGCA
    .         .       5000        .         .

MetAlaGlyTyrProAspProGlyAlaAlaAlaAlaAlaProProAlaAlaArgValPro
ATGGCGCAGTATCCGGACCCCGGCGCGGCGGCGGCTGCCCCGCCGGCGGCGCGCGTGCCG
    .         .         .         .         .         .
```

FIG. 1K

AspThrLeuMetGlnSerLeuAlaValAsnTrpArg***

GACACGCTGATGCAGTCCCTGGCTGTCAACTGGCGCTGAAGCGCCGTGAATCACGGCCCG
      .      5100      .      .      .      .

CCTGCCTCGCGCGGCGGCGCCGTCTCTTTGCGTTCTTCTCCGAGGTATTTCCCATCATGA
      .      .      .      .      .      5200

CGTCGCCCGCGGCGCAATGCGCCAGCGTGCCCGATTCCGGGTTGCTCTGCCTGGTCATGC
      .      .      .      .      .      .      .

TGGCTCGCTATCACGGATTGGCAGCCGATCCCGAGCAGTTGCGGCATGAGTTCGCCGAGC
      .      .      .      5300      .      .

AGGCATTCTGTAGCGAAACGATACAGCCTGGCGGCGCGCCGGGTCGGCCTGAAAGTGCGG
      .      .      .      .      .      .

CGGCACCGACCCGCGCCGGCGCGGCTGCCACGCGCGCCGCTGCCGGCCATCGCGCTGGAC
      5400      .      .      .      .

CGGCAGGGCGGCTACTTTGTT

FIG. 1L

USE OF ADENYLATE CYCLASE OR BACTERIA PRODUCING IT AS VACCINES AGAINST *BORDETELLA*

This is a division of application Ser. No. 09/771,599, filed Jan. 30, 2001, now abandoned which is a continuation of U.S. application Ser. No. 07/926,021, filed Aug. 7, 1992, issued Apr. 10, 2001, as U.S. Pat. No. 6,214,356, which is a continuation of U.S. application Ser. No. 07/623,706, filed Jan. 14, 1991, now abandoned which is a 371 of PCT/FR90/00337, filed May 11, 1990, which claims priority to FR 89 06321, filed May 12, 1989, the disclosures of all of which are incorporated herein by reference.

The invention relates to vaccines capable of protecting man or animals against lethal infections caused by the *Bordetella*. It relates, in particular, to the use of vaccinating preparations developed from *Bordetella* or more particularly from adenylate cyclase produced by these bacteria as protective antigens against the toxic effects of the infections due to *Bordetella*.

It is known that the *Bordetella*, more particularly *Bordetella pertussis*, *Bordetella parapertussis* and *Bordetella bronchiseptica*, are responsible for respiratory diseases in the vertebrates.

Thus, in man, *B.pertussis* is responsible for whooping cough, an infantile disease very wide spread throughout the world.

The vaccination against whooping cough has hitherto been most usually carried out with the aid of inactivated whole bacteria.

However, such vaccines are not always devoid of toxicity in view of the fact that the virulence factors are constituted by proteins secreted by the bacteria and not by the bacteria themselves. The proteins can thus exert serious pathological effects, even after the death of the bacteria.

Among the determinants of virulence of *B.pertussis*, mention should be made of the adhesins such as the agglutinogens (AGG), the filamentous hemagglutinin (FHA) and the pertussis toxin (PTx), a cytotracheal toxin (CTT), a dermonecrotic toxin (DNT) and an adenylate cyclase-hemolysin (AC). The latter is synthesized in the form of a large precursor of 1706 residues. The amino-terminal part of the molecule bears the adenylate cyclase activity and the carboxy-terminal part possesses a strong homology with the Hly gene product of *E.coli* (hemolysin). This adenylate cyclase has the property of being activated by calmodulin.

The research for more suitable methods of prevention has led the inventors to study the role of each of the determinants of virulence and to develop an experimental model of infection mimicking the process of the natural disease.

These studies have made it possible to note the role of adenylate cyclase as cytotoxin and as protective antigen, and to develop a novel use of the vaccinating preparations based on adenylate cyclase or bacterial preparations producing adenylate cyclase.

The invention relates more particularly to the use of a bacterial vaccinating preparation developed from a given bacterium of the *Bordetella* genus, this use being characterized in that it is used to protect man or animals against the infections and the toxic effects caused by a bacterium of the *Bordetella* genus but different from that of the vaccinating preparation.

In accordance with another feature, the invention also relates to the use of a vaccinating preparation developed from an adenylate cyclase of a given bacterium of the *Bordetella* genus in order to protect man or animals against the infections and the toxic effects caused by a bacterium of the *Bordetella* genus different from that from which the adenylate cyclase is derived.

The bacteria of the *Bordetella* genus are selected from *B.pertussis*, *B.parapertussis*, and *B.bronchiseptica*.

In a preferred embodiment of the invention, the vaccinating preparation is developed from *B.bronchiseptica* or from the adenylate cyclase of *B.bronchiseptica* and is used to provide protection against the infections and the toxic effects caused by *B.pertussis* or *B.parapertussis*.

It should be noted that this crossed protection obtained starting from strains of *B.bronchiseptica* offers the advantage of using strains with more rapid growth than *B.pertussis* or *B.parapertussis* in order to develop vaccines against the infections caused by *B.pertussis* or *B.parapertussis*.

According to another embodiment of the invention, the vaccinating preparation is developed from *B.pertussis* or the adenylate cyclase of *B.pertussis* and is used to provide protection against the infections and the toxic effects caused by *B.bronchiseptica* or *B.parapertussis*.

According to yet another embodiment of the invention the vaccinating preparation used is developed from *B.parapertussis* or the adenylate cyclase of *B.parapertussis* and is used to provide protection against the infections and the toxic effects caused by *B.pertussis* or *B. bronchiseptica*.

According to yet another embodiment of the invention, the vaccinating preparation used is developed from *B.parapertussis* or the adenylate cyclase of *B.parapertussis* and is used to provide protection against the infections and the toxic effects caused by *B.pertussis* or *B.bronchiseptica*.

The adenylate cyclase of the *Bordetella* to which reference has been made above is an adenylate cyclase such as that obtained by placing a supernatant of a bacterial culture of *Bordetella* in contact with an Affigel-calmodulin$^R$ gel.

More particularly, it is a preparation of adenylate cyclase such as those described in the application FR 2606789 filed on Nov. 17, 1986.

It will be recalled that these preparations are characterized in that they possess a high purity and are almost completely devoid of contaminating bacterial products, in particular pertussis toxins, lipopolysaccharide (or LPS) and filamentous hemagglutinin (or FHA).

The adenylate cyclase of these preparations exists in a homogeneous form sedimenting on a sucrose density gradient with a coefficient S equal to 3.6. It exists in two structurally related, molecular forms of 45 and 43 kDa respectively.

Such preparations of adenylate cyclase possess an activity which may attain and even exceed 1600 μmole of cAMP min$^{-1}$ mg$^{-1}$.

Such preparations may be prepared from bacterial cultures expressing the AC (adenylate cyclase), more particularly from pathogenic bacteria whose AC is capable of interfering with the AC of eucaryotic cells, by placing a supernatant of bacterial cultures expressing the adenylate cyclase and concentrated beforehand or an extract of these bacteria in contact with calmodulin.

In order to obtain the enzyme in the free form, calmodulin fixed to a support is used, then the absorbed enzyme is recovered with the aid of a denaturing agent which is removed in turn, and the preparation of the free enzyme is recovered.

The support is more particularly constituted by a material inert with respect to the preparation containing the enzyme, and is capable of retaining molecules of high molecular weight, such as a gel or a filtering material.

The filtering material is advantageously made of nitrocellulose or a plastic material and exhibits a porosity of 0.45–0.22 µm.

The denaturing agent is preferably urea and preferably 4 to 8.8 M.

The concentrated supernatant of the bacterial culture is obtained by subjecting a supernatant of bacterial cultures expressing the AC to one or several filtration steps with the aid of nitrocellulose filters or filters of plastic material of porosity advantageously from 0.45 to 0.22 µm, then by incubating the filters with a detergent in order to release the AC and by removing from the AC preparation the insoluble materials present.

The detergent is, for example, TRITON® or NP40®.

The bacterial extract is obtained by treatment of bacterial cells expressing the adenylate cyclase with urea and recovery of the supernatant.

As a variant, an adenylate cyclase is used such as that expressed by the nucleotide sequence given in the only figure with the corresponding amino acid sequence.

It will be obvious that the bases of the nucleotide sequence under consideration may be in an order different from that found in the genes and/or that these bases may be, where appropriate, substituted provided that a probe developed from such a sequence gives a characteristic and unequivocal response with regard to the capacity to recognize the presence of a gene coding for a protein with adenylate cyclase activity.

Any nucleotide sequence which can hybridize with this chain sequence such as that obtainable by reverse enzymatic transcription of the corresponding RNA or also by chemical synthesis is also included in the framework of the invention.

The above vaccinating preparations used may or may not be combined with the FHA and/or the PTx in the same inoculum.

In this latter case, the FHA is administered at the same time as the vaccinating preparation or at a different time. The preparations of FHA are advantageously obtained, for example, according to the method of SATO et al in Infect. Immun., 1983, 41, 310–320 or that of IMAIZUMI et al in Journal of Microbiol. Methods, 2, 334–347 (1984).

In accordance with another feature, the invention relates to vaccines capable of inducing a protection against the toxic effects and the infections caused by the *Bordetella*, molecular vaccines containing at least the active part of the amino acid sequence represented in the only figure, where appropiate, combined or not in the same inoculum with the FHA and/or the PTx.

These vaccines are advantageously used in conformity with the invention in order to carry out crossed protections.

In the implementation of the invention, the vaccinating preparations based on bacteria or the adenylate cyclase, advantageously purified, produced by these bacteria as well as the vaccines developed from recombinant adenylate cyclase are used at the usual doses and in the usual forms of administration, in particular in the standard forms which can be administered by the intranasal, oral or parenteral routes.

Other characteristics and advantages of the invention will become apparent in the description of the examples which follow and by referring to the only figure which shows the nucleotide sequence of the active part of the gene of *B.pertussis* coding for the adenylate cyclase and the corresponding sequence of amino acids.

The model of respiratory infection used in the assays reported in the examples is a model of infection by the intranasal route. The in vivo selection from a mouse lung infected by *B.pertussis* of a hyperpathogenic derivative of the virulent strain of *B.pertussis* 18323S (international reference strain for the evaluation tests of vaccines) has made it possible to observe in the adult mouse, after injection of bacteria by the intranasal route, an acute hemorrhagic edematous alveolitis (AHEA), lethal within 48–72 h.

The analyses of the products of the examples are performed as follows.

The activity of the AC is measured according to the method of White A. A. in Methods Enzymol., 38C, 41–46, 1974, as modified by Hanoune et al (J. Biol. Chem., 252, 2039–2046, 1977).

The activities of PTx and FHA are measured according to the method of TUOMANON S. and WEISS A. in J. Inf. Dis., 152, 118–125, 1985.

EXAMPLE 1

Figure 1A:
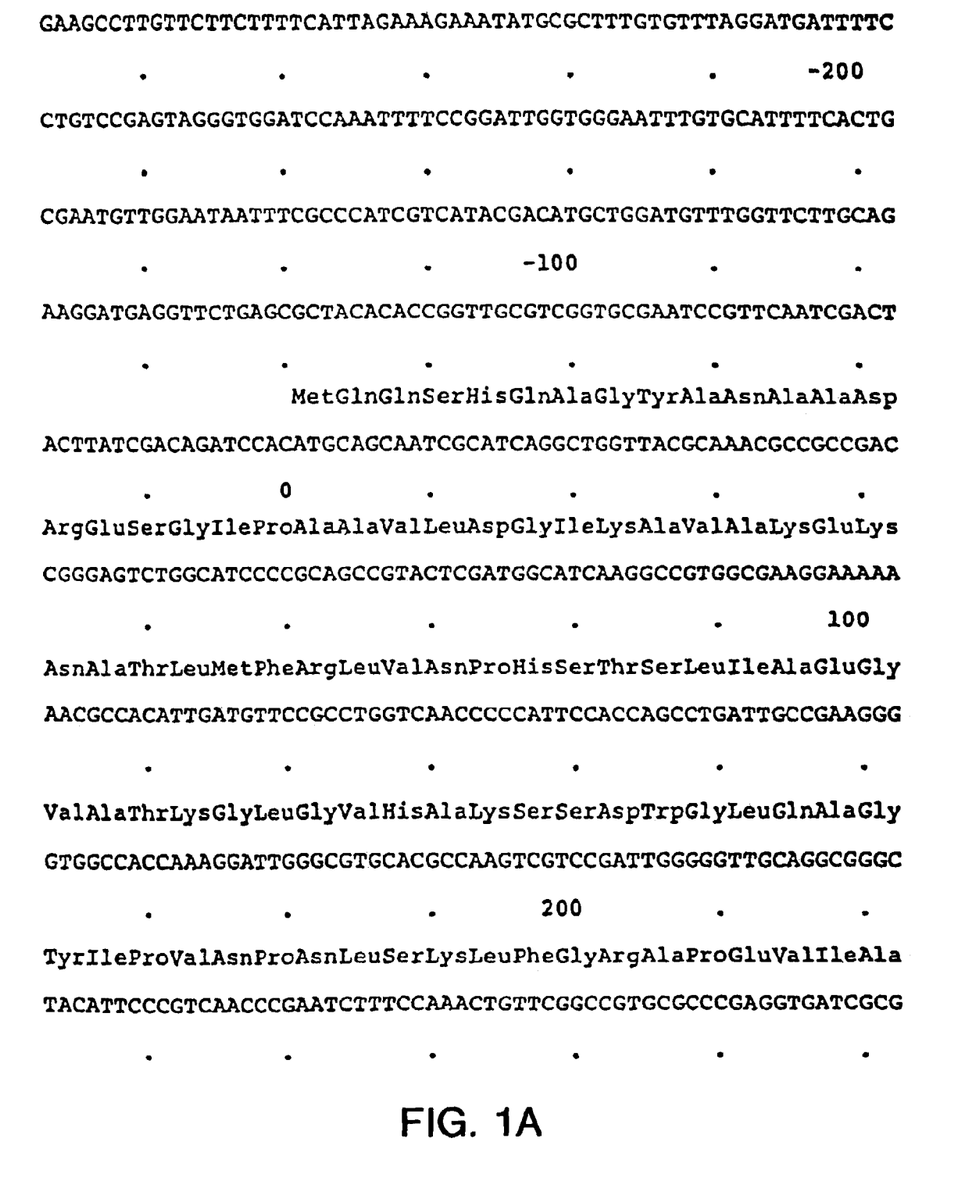
FIGS. 1A to 1L show the nucleotide sequence of the active part of the gene of *B. pertussis* coding for the adenylate cyclase and the corresponding sequence of amino acids.
Figure 1B:
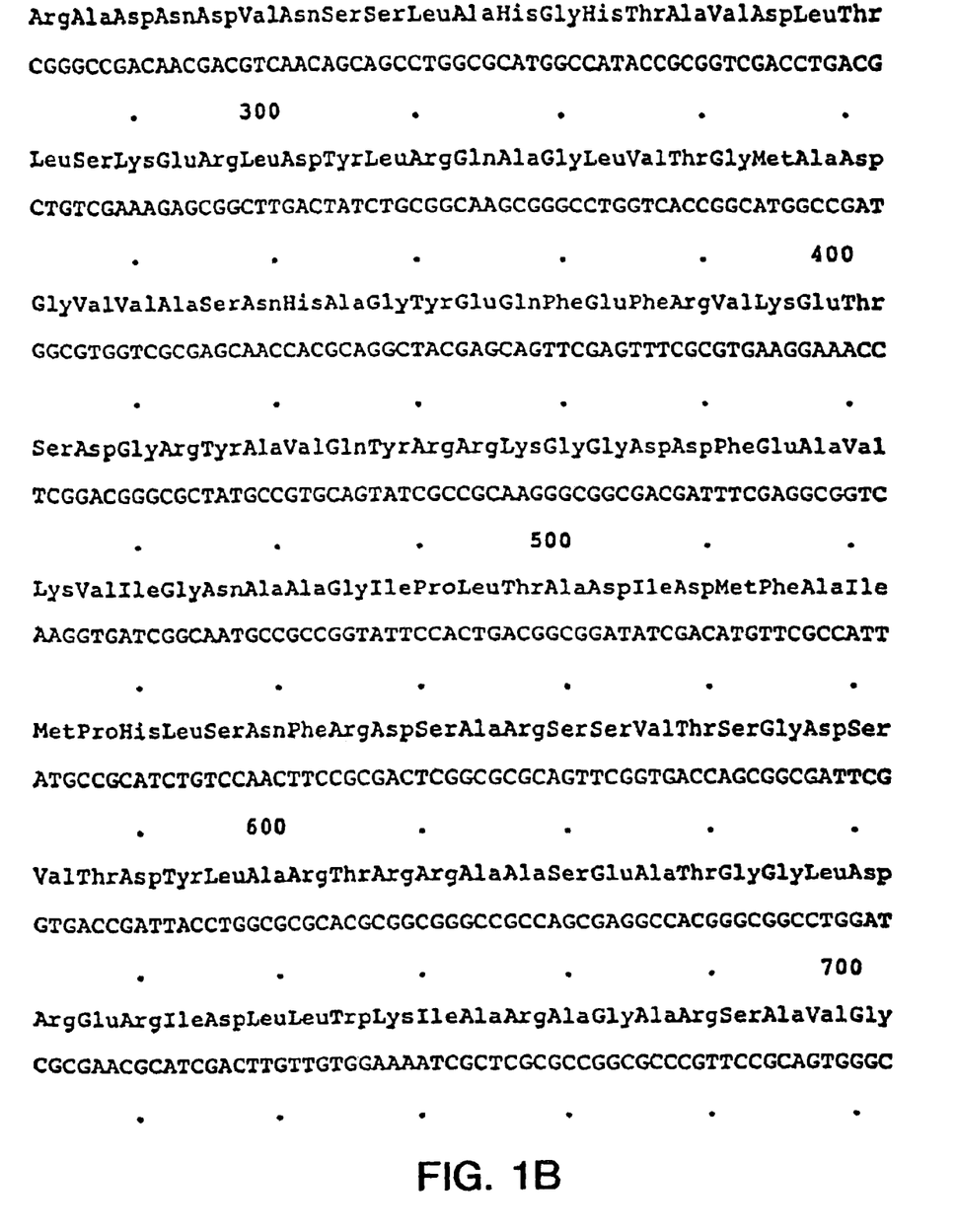
Figure 1C:
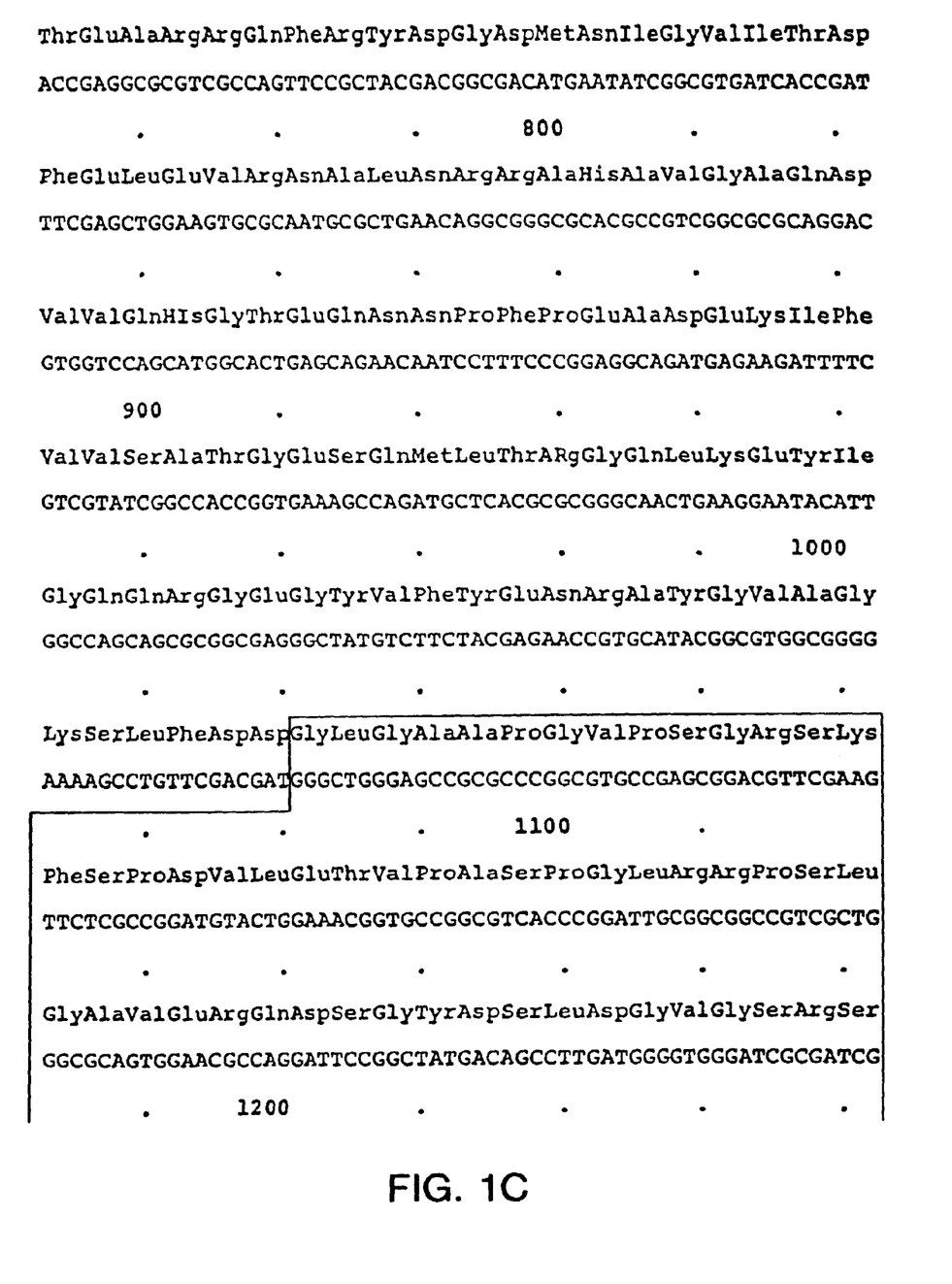
Figure 1D:
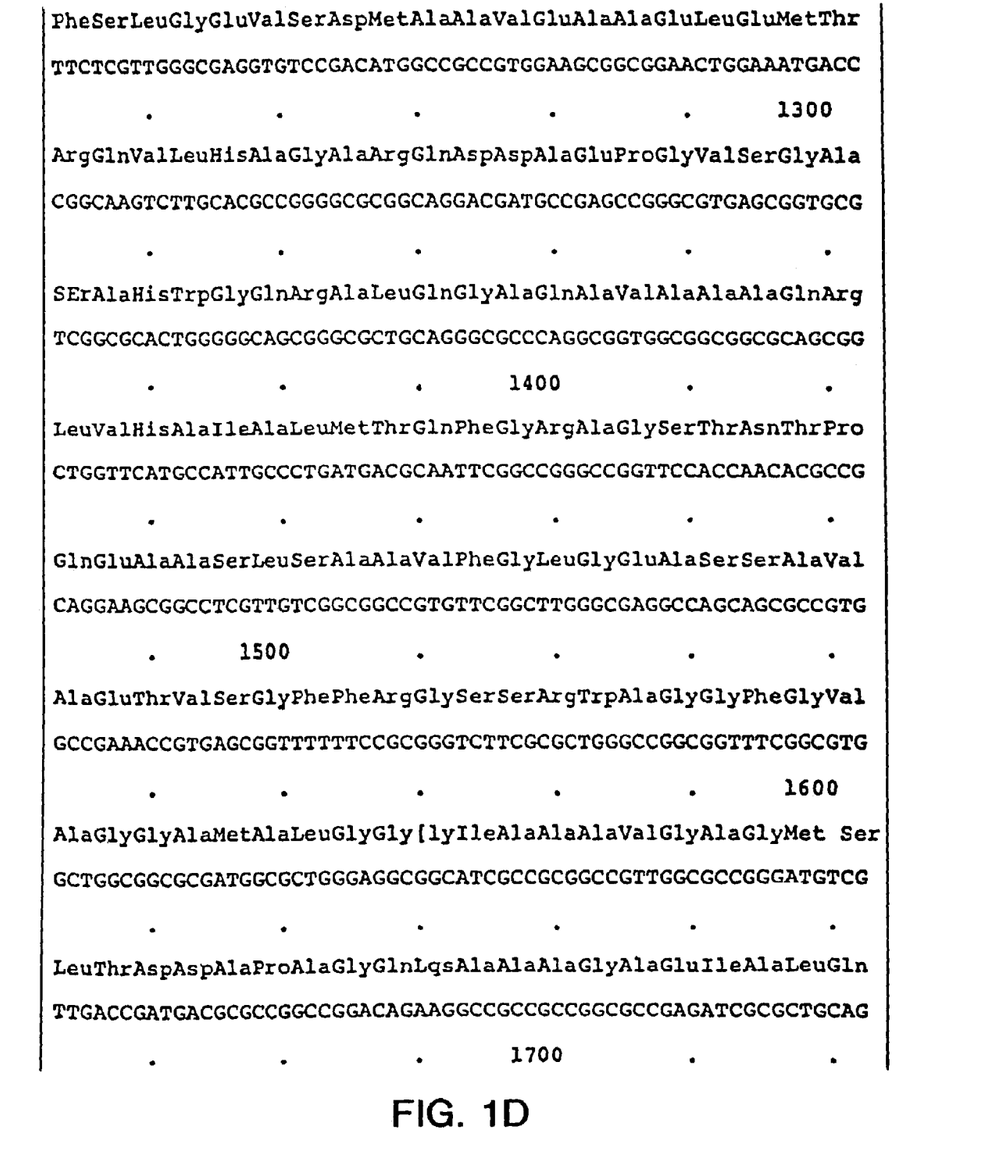
Figure 1E:
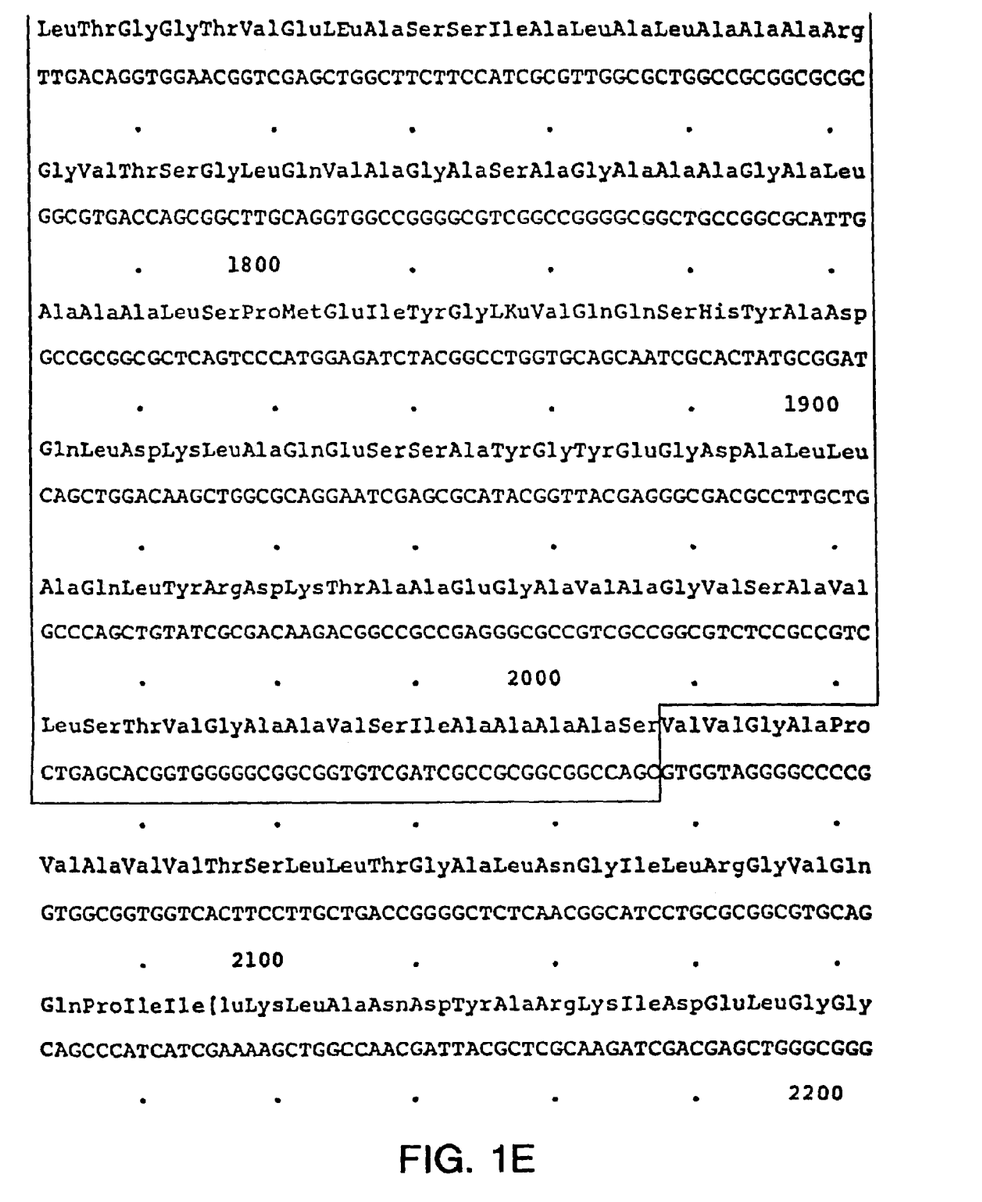
Figure 1F:
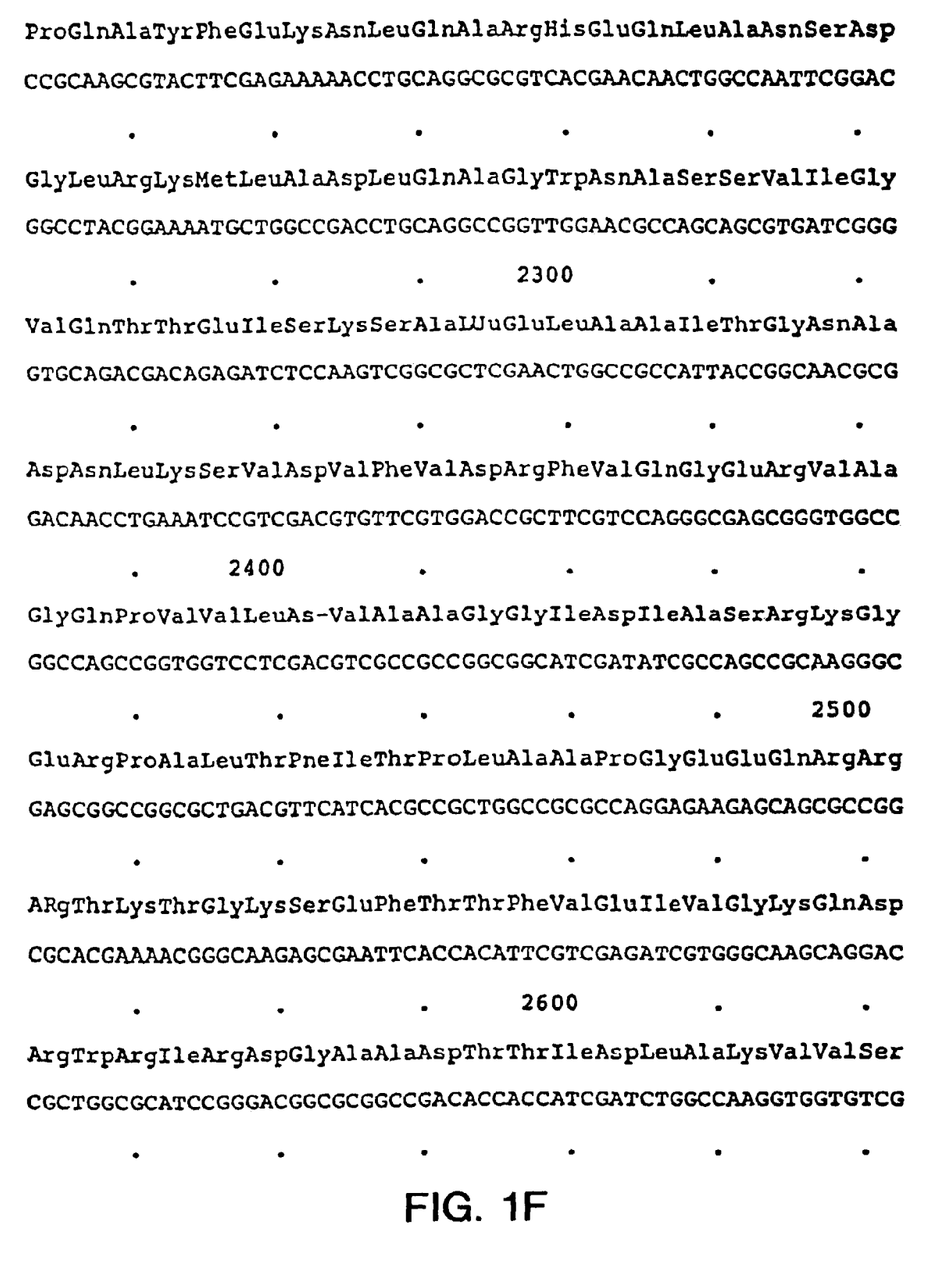
Figure 1G:
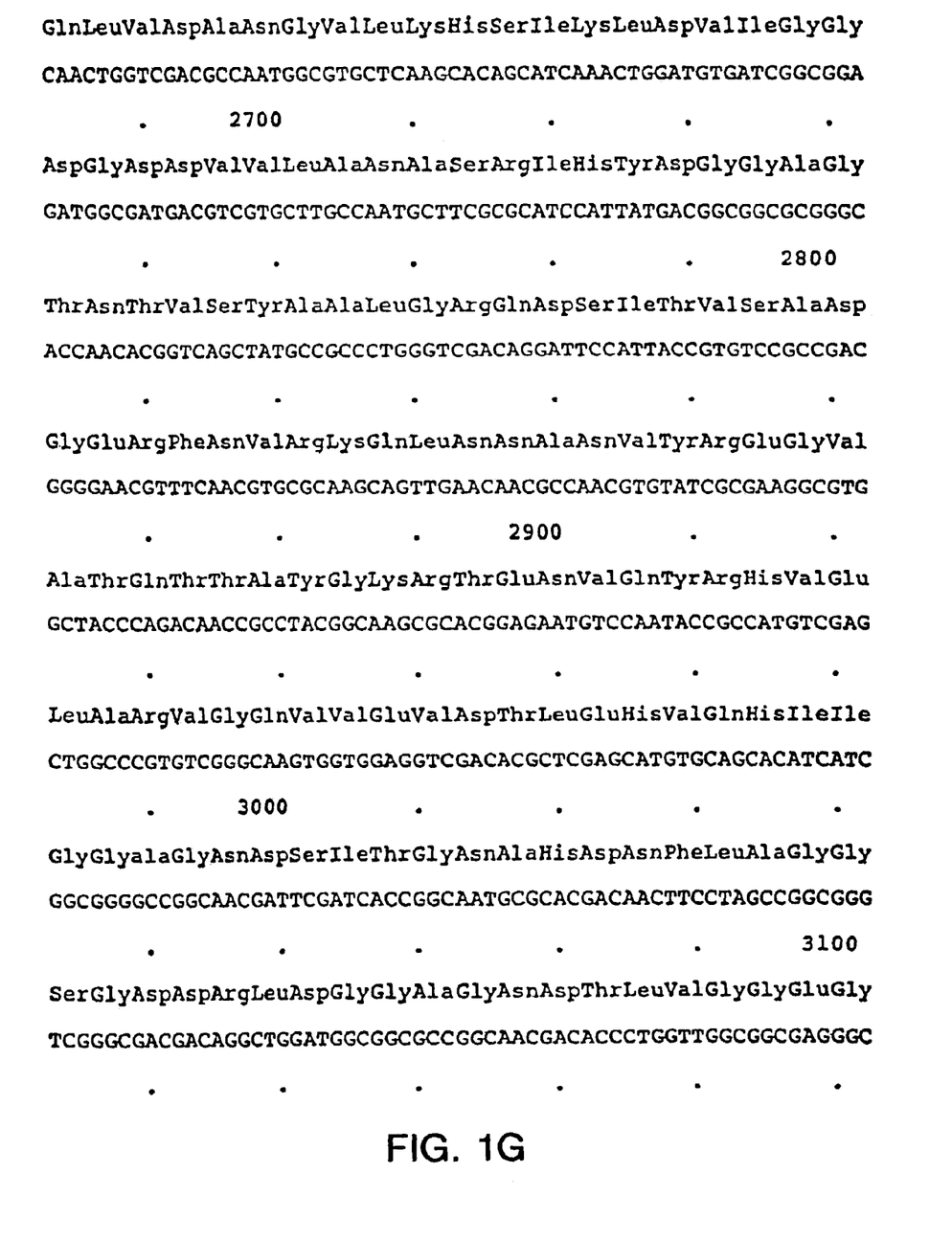
Figure 1H:
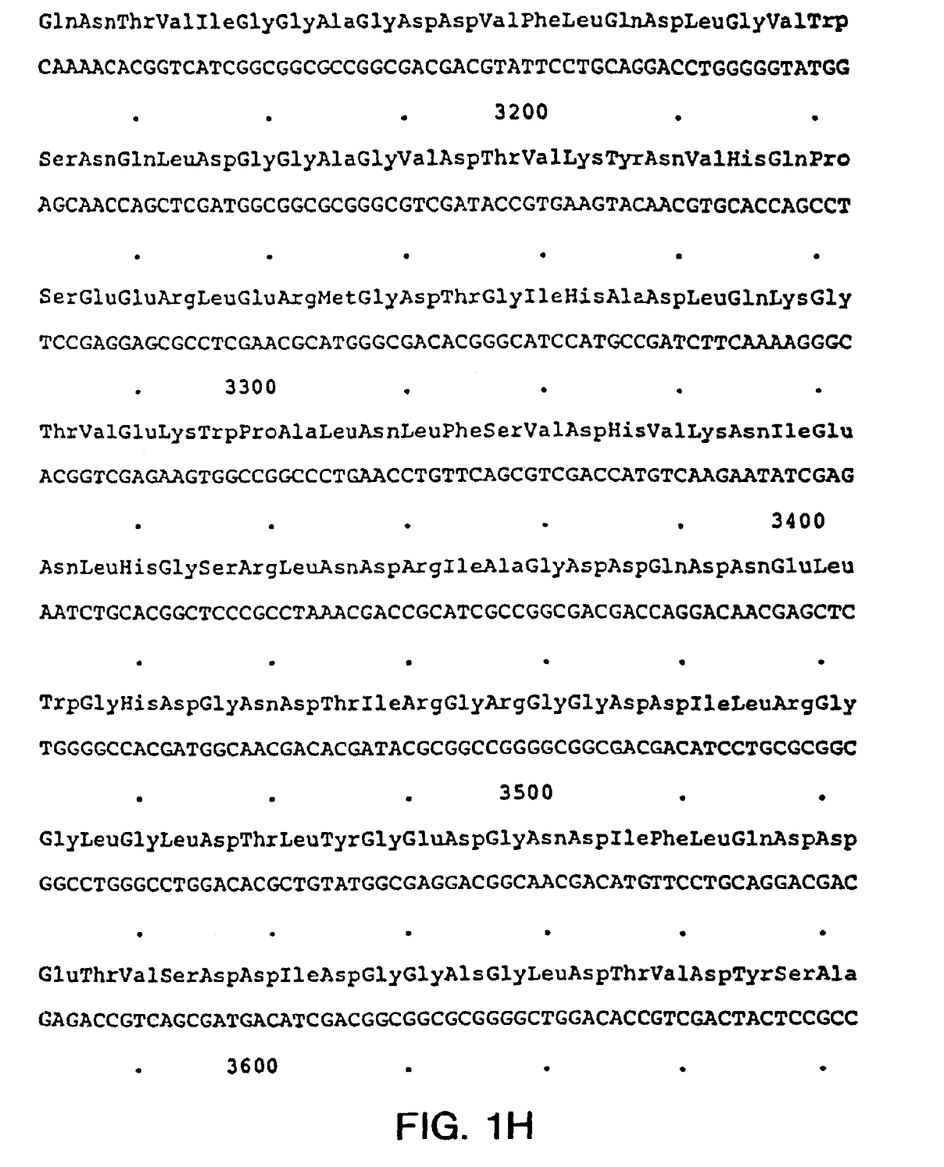
Figure 1I:
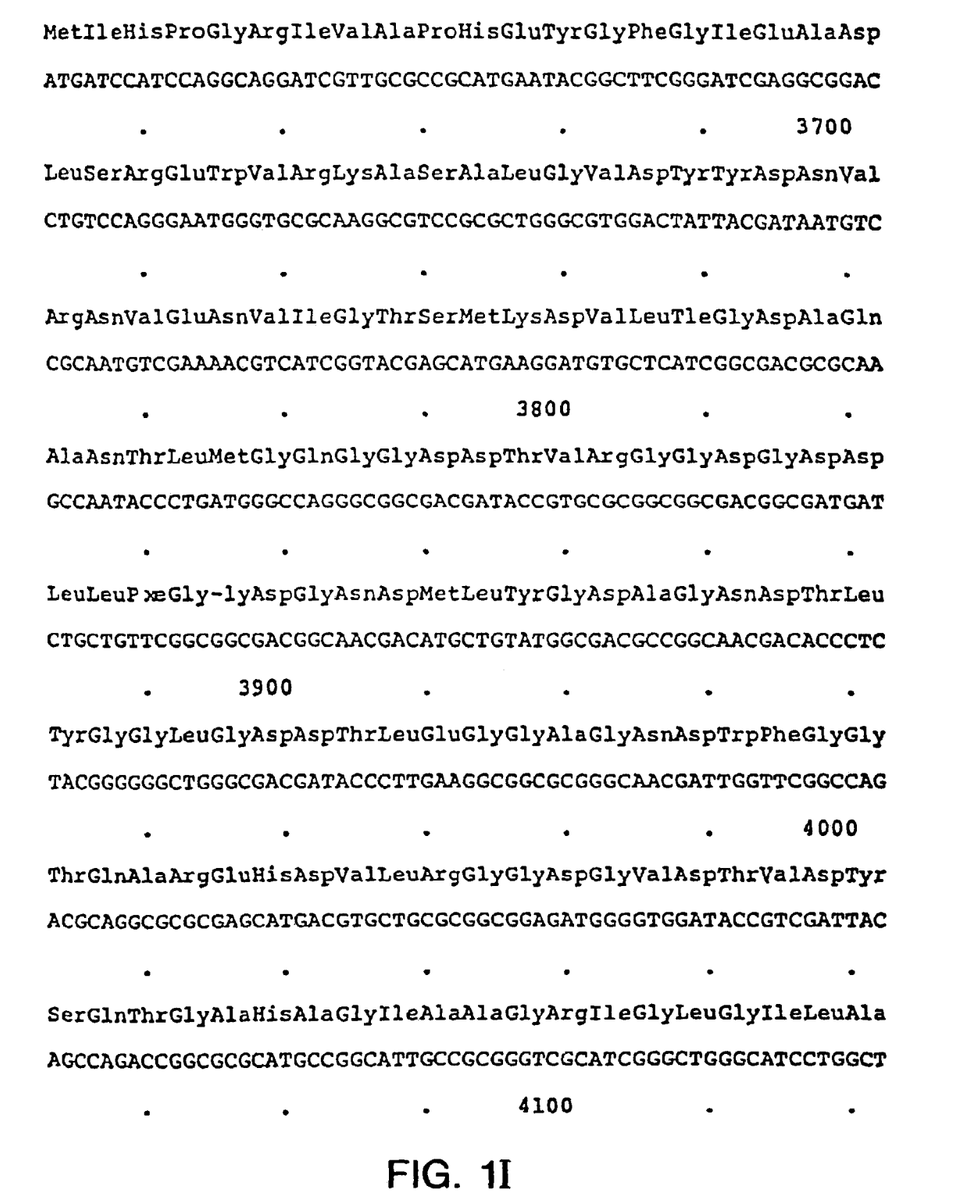
Figure 1J:
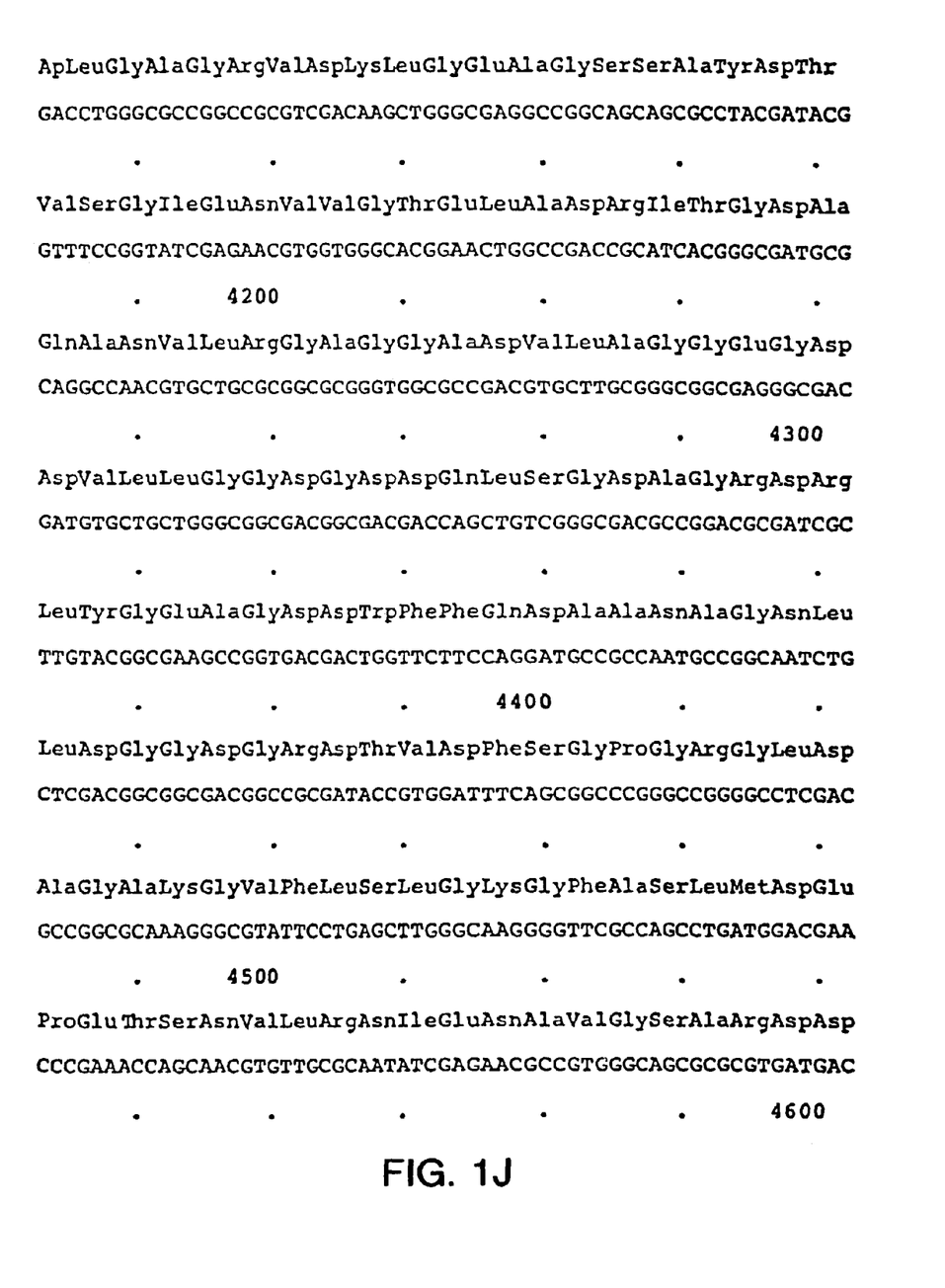
Figure 1K:
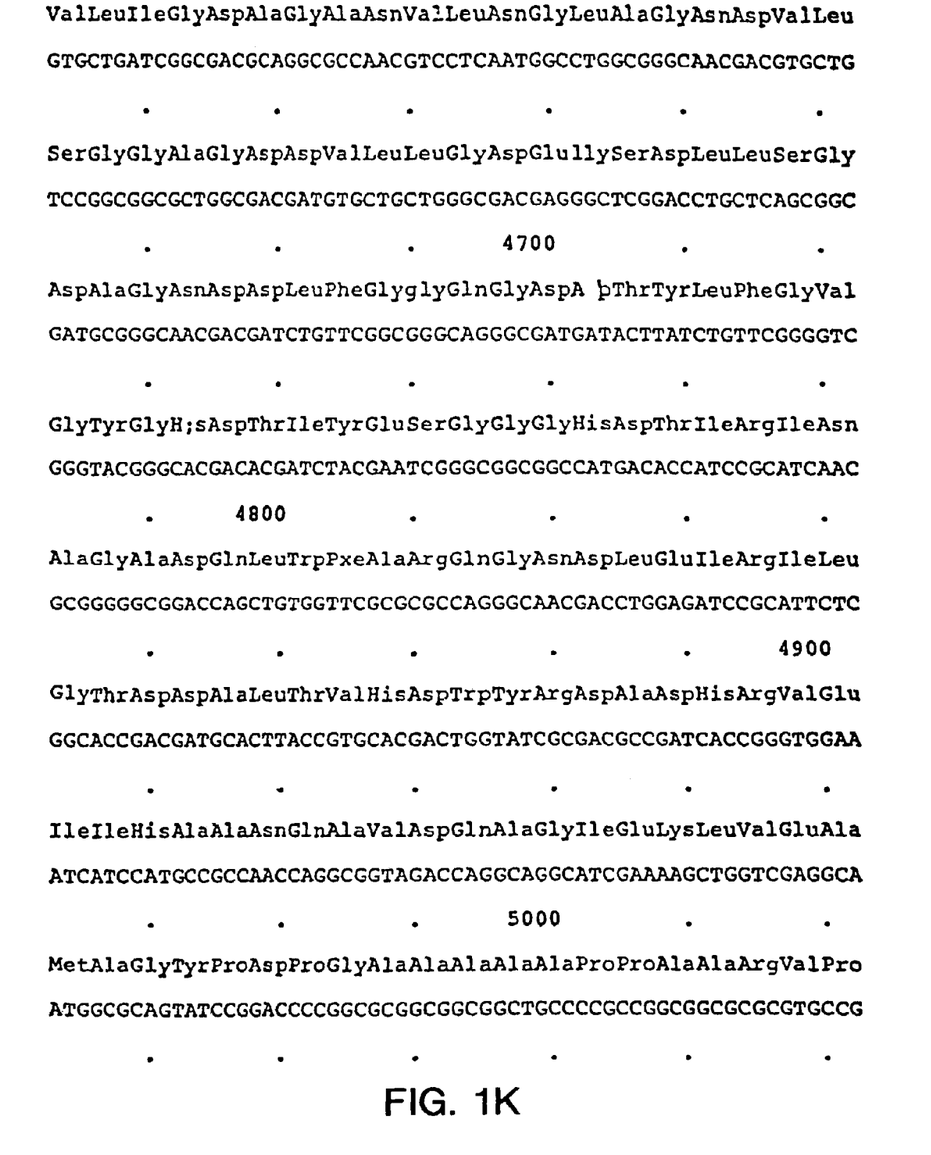
Figure 1L:
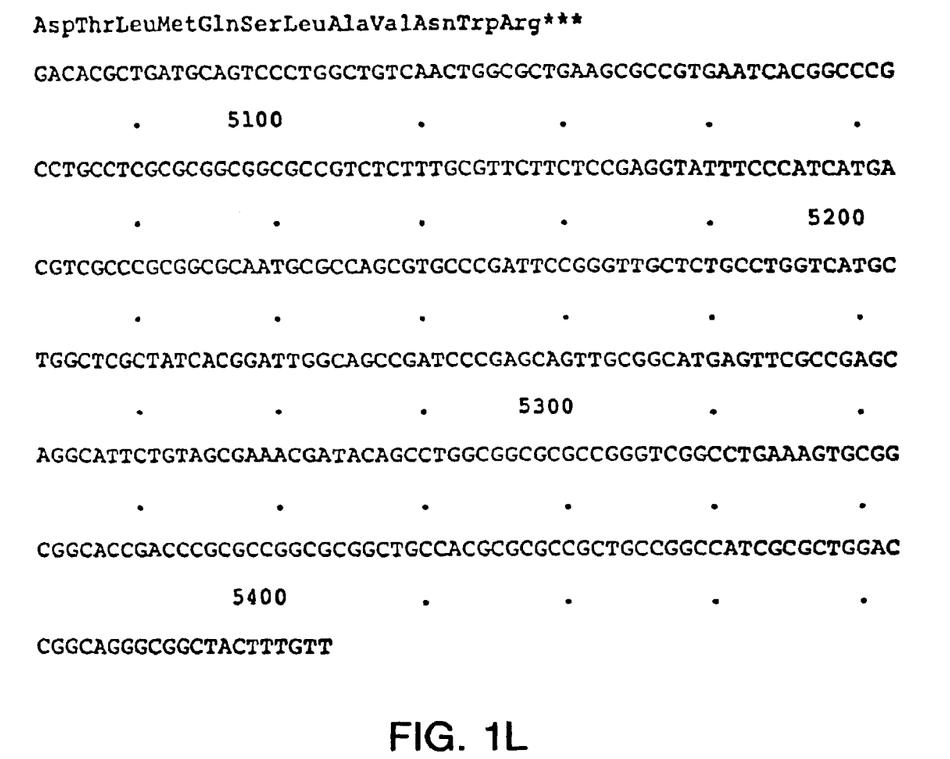

Culture of *B.bronchiseptica* and Isolation of a Supernatant With a High Concentration of Adenylate Cyclase A preculture of *B.bronchiseptica* 9.73, phase I and a spontaneously avirulent, stable variant of this strain, phase IV are grown for 48 hours at 36° C. on a modified Stainer-Scholte agar medium supplemented with cyclodextrin (according to IMAIZUIMI et al in J. Chim. Microbiol., 17, 781–786, 1983). The preculture is then transferred to a modified Stainer-Scholte liquid medium without cyclodextrin. The *B.bronchiseptica* 9.73 strain was isolated from the nostrils of a hare.

The liquid cultures are stirred at 150 rev./min. for 15 hours at 36° C. in a 1 liter Erlenmeyer containing 250 ml of medium. The culture is continued until an optical density $OD_{650}=1.2\pm0.2$ is obtained. The bacteria are then removed by centrifugation at 5000×g for 25 min.

The culture supernatants are stored at −30° C. until used or are concentrated immediately.

For the purposes of concentration, 3 liters of culture supernatant containing about 10 µg of proteins and 0.1 unit of enzyme per ml are filtered on filters of the MILLIPORE® HAWP type of 0.45 µm. In this way, more than 90% of the enzymatic activity is retained on the filters. About 80% of this activity can be recuperated by incubation of the filters in 40 ml of a buffer A constituted by 50 µM Tris-HCl, pH 8 containing 6 µM of $MgCl_2$ and 0.1% of TRITON X-100®. The insoluble material is removed by centrifugation for 30 mm. at 15000×g at 40° C. The specific activity of the concentrated culture supernatant is 115 units per milligram of protein.

A bacterial suspension of the strain 9.73 was injected into a mouse by the intranasal route; 48 hours later the lungs were excised and ground and a hemolytic clone was isolated, namely the clone 9.73S. This clone was deposited on 12 May 1989 with the CNCM under the No. I-858. This clone is hemolytic and synthesizes large amounts of adenylate cyclase. A bacterial suspension of this clone causes hemorrhagic edema in the lung of the mouse.

EXAMPLE 2

Procedure for the Isolation of Purified Extra-cytoplasmic Adenylate Cyclase in the Free Form 40 ml of concentrated culture supernatant are added to 0.8 to 1 ml of AFFIGEL-CALMODULIN® and the mixture is stirred slowly at 40° C. for 18 hours. More than ⅔ of the enzymatic activity is retained on the gel.

The AFFIGEL-CALMODULIN® is sedimented by centrifugation at 300×g for 1 minute, it is washed several times with 0.5 M NaCl in buffer A. The adenylate cyclase is recovered from the gel with the aid of 2.5 ml of 8.8 M urea in buffer A. The urea is removed by filtration on a column of SEPHADEX G-35®, equilibrated with buffer A.

This enzymatic preparation possesses a specific activity of 1100 units/mg of protein.

It may be stored at −80° C. without loss of activity for several weeks.

EXAMPLE 3

Procedure for the Isolation of Purified Adenylate Cyclase from Bacterial Extracts A bacterial culture expressing AC activatable by calmodulin is subjected to a treatment with 8M urea for about 2 hours at room temperature. The supernatant which constitutes the bacterial extract is recovered and it is placed in contact with the Affigel-calmodulin gel under the conditions mentioned above.

An enzymatic preparation of high purity is obtained exhibiting approximately the same specific activity.

EXAMPLE 4

Study of the Secretion of AC, PTx and FHA, and the LD50 of *Bordetella* Strains.

In table 1 below, are presented the results obtained by determine the factors of virulence AC, PTx and FHA and by measuring the LD50 (dose killing 50% of the mice in a batch) of different strains of *Bordetella*.

They are strains of *B.pertussis* (BP), *B.parapertussis* (BPP) and *B.bronchiseptica* (BB) corresponding either to hyperpathogenic strains, which secrete large amounts of adenylate cyclase (these strains bear the reference S in the table), or to parental strains of the hyperpathogenic strains.

TABLE 1

| | AC | PTx | FHA | LD50 |
|---|---|---|---|---|
| BP18323 | 20 | 1 | 2 | 3 $10^8$ |
| BP18323S | 180 | 4 | 2 | $10^8$ |
| BR8114 | 2 | (+) | | |
| BP8144S | 6 | (+) | | |
| BP8132 | 1 | (+) | 32 | 3.2 $10^8$ |
| BP8132S | 3 | (+) | 32 | <1.2 $10^8$ |
| BPP632 | 8 | — | 64 | 2 $10^8$ |
| BPP632S | 35 | — | 64 | <$10^8$ |
| BB973S | 110 | — | 16 | 4 $10^6$ |

These results reveal the high production of adenylate cyclase by hypopathogenic strains, more particularly by *B.bronchiseptica* 973S and *B.pertussis* 18323S.

The secretion of PTx is also increased in the hyperpathogenic derivatives as the results relating to *B.pertussis* show whereas the secretion of FHA remains the same in the two strains.

*B.bronchiseptica* and *B.parapertussis*, which synthesize the same factors as *B.pertussis* with the exception of the PTx, induce a hemorrhagic edematous alveolitis in the mouse similar to that induced by *B.pertussis*. On the other hand, a strain derived from the virulent strain *B.pertussis* 8132, the strain B.P.348 accommodating a transposon Tn5 in the structural gene of the AC, inactivating the latter, is incapable of inducing a AHEA in the mouse. Nonetheless, this mutant secretes all of the other factors of virulence, in particular the PTx.

The body of these results designates the AC as the factor responsible for the hemorrhagic edematous alveolitis in the mouse.

EXAMPLE 5

1. Experiments of Active Protection Starting from Bacterial Vaccines

Protection experiments (against *B.pertussis*) were carried out with the aid of different bacterial vaccines (usually 3 sub-cutaneous injections of 250 μl of a bacterial suspension containing $10^9$ bacteria/ml, heated to 56° C. at weekly intervals).

In table 2 below are reported the results obtained by using strains of *B.bronchiseptica* 9.73S as well as strains of *B.pertussis* 18323S, *B.parapertussis* 63.25 and *B.avium* (Blike Hewouet) for the development of the bacterial vaccines.

The *B.pertussis* strain is administered two weeks after the last immunization: 50 μl of $10^8$ live bacteria of the *B.pertussis* 18323S strain are injected by the intranasal route.

| STRAIN INJECTED | LETHAL TEST (*B. pertussis*) |
|---|---|
| 0 | 10/10 |
| *B. bronchiseptica* | 0/10 |
| *B. pertussis* | 0/10 |
| *B. parapertussis* | 3/10 |
| *B. avlum* | 9/10 |

It will be noted that the mice vaccinated with the aid of preparations of *B.bronchiseptica* are completely protected against the lethal test with *B.pertussis* (crossed protection), like those vaccinated with *B.pertussis*.

On the other hand, the mice vaccinated with preparations of *B.avium* are not protected, which works in favour of the role of the AC in the induction of hemorrhagic edematous alveolitis.

2. Experiments of Active Protection Starting from Purified Antigens

Purified antigens are used.

The preparations of AC are purified either from the culture supernatant (70% of the enzyme is excreted by the bacterium), or from the bacteria by working advantageously according to the procedure of the patent application FR 2606789 of Nov. 17, 1986.

Mice were immunized with different doses of antigen (3 sub-cutaneous injections of 250 μl of antigen in 10 mM Tris buffer, pH 7, containing 1 mg/ml of $Am^{+++}$ at weekly intervals) before the lethal test with *B.pertussis* was made.

For the lethal test, 50 μl of a bacterial suspension of the virulent and hyperpathogenic strain 18323S is injected by the intranasal route 2 weeks after the last immunization. The bacterial concentration of the suspension is $10^8$ in test a, $2 \times 10^8$ in test b, and $10^7$ in test c.

In table 3 below, the results are reported of the protection obtained against a strain of *B.pertussis* (BP 18323S) at different concentrations after injection of AC, recombinant AC of a vaccine, PTx and FHA.

The recombinant AC is advantageously such as described in the patent application FR 2621597 of Jul. 24, 1987. It is a fragment corresponding to the structural gene of the AC which could be expressed in *E.coli*. This fragment, which bears the adenylate cyclase activity and the binding site for calmodulin, was purified to homogeneity (see the figure).

| AC | $AC_{rec}$ | VACCIN | PTx | FHA | 0 |
|---|---|---|---|---|---|
| | a: lethal test B.P. 18323S 10/LD50 | | | | |
| 3/0.9 μg | 3/1.5 μg | 3/$10^9$b | 2/2 μg | 2/10 μg | |
| 9/12 | 1/10 | 0/40 | 9/22 | 20/22 | 20/22 |
| | b: lethal test B.P. 18323S 20/LD50 | | | | |
| 3/2 μg | | 3/$10^9$b | | | |
| 5/10 | | 3/10 | | | 10/10 |
| | c: lethal test B.P. 18323S 1/LD50 | | | | |
| 3/6 μg | 3/6 μg | 3/18 μg | 3/2 μg | 3/10 μg | |
| 0/10 | 0/10 | 0/10 | 0/10 | 5/10 | 5/10 |

The results of lethality are expressed as the number of dead mice over the total number of mice.

The results obtained show the production of a synthesis of anti-AC antibodies and a protection of the mice after immunization with AC (three immunizations of 1.5 μl of AC). This protection is almost complete when the lethal test is performed with a number of bacteria equal to ($10^7$ live bacteria) or 10 times higher than the lethal dose 50 ($10^8$ live bacteria); it is 60% when the lethal test is performed with a number of bacteria equal to 20 times the lethal dose 50 ($2.10^8$ lethal bacteria).

Complete protection was obtained after immunization of mice with the recombinant AC when the lethal test was performed with a number of bacteria equal to the lethal dose 50. The immunizations performed with FHA did not show a protective effect of this toxin in spite of the presence of antibodies in the mice immunized even when the lethal test was performed with a small number of bacteria.

The experiments conducted with the PTx show a partial protection after two immunizations with 2 μg of PTx when the lethal test is 10 times higher than the lethal dose 50 but it must be pointed out that, in this case, the synthesis of anti-PTx antibodies is very low. When the mice are immunized with 3 times 2 μg of PTx, the synthesis of antibodies is much greater and we obtain complete protection when the lethal test is performed with a number of bacteria equal to the lethal dose 50.

In sum, these results show that the adenylate cyclase constitutes the cytotoxin responsible for the hemorrhagic edematous alveolitis observed in the mouse infected by *B.pertussis* and constitutes an antigen protecting against such lesions. The PTx and the FHA would appear to play no role in the induction of this AHEA but could be protective antigens of such lesions by inhibiting the adhesion of bacteria to the respiratory epithelium.

The invention claimed is:

1. A method for protecting against the toxic effects of infection by a first *Bordetella* species in a mammal, comprising:
    administering to said mammal a preparation comprising purified adenylate cyclase of a second *Bordetella* species in an amount sufficient to protect against the toxic effects of said first *Bordetella* species, wherein:
    (a) said purified adenylate cyclase exhibits a specific activity of greater than or equal to about 115 μmole cAMP/min/mg protein;
    (b) said purified adenylate cyclase sediments on a sucrose density gradient with a coefficient S equal to 3.6 and has a molecular weight of 43 or 45 kDa;
    (c) said first *Bordetella* species is *Bordetella pertussis*; and
    (d) said second *Bordetella* species is *Bordetella bronchiseptica*.

2. A method for protecting against the toxic effects of infection by a first *Bordetella* species in a mammal, comprising:
    administering to said mammal a preparation comprising purified adenylate cyclase of a second *Bordetella* species in an amount sufficient to protect against the toxic effects of said first *Bordetella* species, wherein:
    (a) said purified adenylate cyclase exhibits a specific activity of greater than or equal to about 115 μmole cAMP/min/mg protein;
    (b) said purified adenylate cyclase sediments on a sucrose density gradient with a coefficient S equal to 3.6 and has a molecular weight of 43 or 45 kDa;
    (c) said first *Bordetella* species is *Bordetella parapertussis*; and
    (d) said second *Bordetella* species is *Bordetella bronchiseptica*.

3. A method for protecting against the toxic effects of infection by a first *Bordetella* species in a mammal, comprising:
    administering to said mammal a preparation comprising purified adenylate cyclase of a second *Bordetella* species in an amount sufficient to protect against the toxic effects of said first *Bordetella* species, wherein:
    (a) said purified adenylate cyclase exhibits a specific activity of greater than or equal to about 115 μmole cAMP/min/mg protein;
    (b) said purified adenylate cyclase sediments on a sucrose density gradient with a coefficient S equal to 3.6 and has a molecular weight of 43 or 45 kDa;
    (c) said first *Bordetella* species is *Bordetella bronchiseptica*; and
    (d) said second *Bordetella* species is *Bordetella pertussis*.

4. The method of any of claims 1, 2, or 3, wherein said purified adenylate cyclase exhibits a specific activity of greater than or equal to about 1100 μmole cAMP/min/mg protein.

5. The method of any of claims 1, 2, or 3, wherein said purified adenylate cyclase exhibits a specific activity of greater than or equal to about 1600 μmole cAMP/min/mg protein.

* * * * *

UNITED STATES PATENT AND TRADEMARK OFFICE
CERTIFICATE OF CORRECTION

| | |
|---|---|
| PATENT NO. | : 7,211,263 B2 |
| APPLICATION NO. | : 10/334796 |
| DATED | : May 1, 2007 |
| INVENTOR(S) | : Nicole Guiso-Maclouf |

It is certified that error appears in the above-identified patent and that said Letters Patent is hereby corrected as shown below:

In claim 2, column 8, line 34, "kDa:" should read --kDa;--.

In claim 3, column 8, line 51, "kDa:" should read --kDa;--.

Signed and Sealed this

Twenty-sixth Day of June, 2007

JON W. DUDAS
*Director of the United States Patent and Trademark Office*